(12) United States Patent
Meng

(10) Patent No.: US 6,800,785 B1
(45) Date of Patent: Oct. 5, 2004

(54) PROCESS FOR THE SYNTHESIS OF ESTROGEN RECEPTOR MODULATORS

(75) Inventor: Dongfang Meng, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/685,719

(22) Filed: Oct. 15, 2003

Related U.S. Application Data

(60) Provisional application No. 60/418,579, filed on Oct. 15, 2002.

(51) Int. Cl.$^7$ .................. C07C 45/45; C07C 49/537; C07C 49/543; C07C 49/547
(52) U.S. Cl. .................. 568/322; 568/315; 568/326; 549/416; 556/436
(58) Field of Search ................ 568/315, 322, 568/326; 549/416; 556/436

(56) References Cited

FOREIGN PATENT DOCUMENTS

WO    WO 2001/82923 A1    11/2001

OTHER PUBLICATIONS

Meng et al, Tet. Letters, 43 (50) , p. 9035–9038 (Dec. 9, 2002).*

Dauben, W.G. and Michno, D.M., "Direct Oxidation of Tertiary Allylic Alcohols. A Simple and Effective Method for Alkylative Carbonyl Transposition," J. Org. Chem., 1997 vol. 42, No. 4, pp. 682–685.

Dolman, S.J., et al., "Efficient Catalytic Enantioselective Synthesis of Unsaturated Amines: Preparation of Small– and Medium–Ring Cyclic Amines through Mo–Catalyzed Asymmetric Ring–Closing Metathesis in the Absence of Solvent", J. Am. Chem. Soc. 2002, vol. 124, pp. 6991–6997.

Furstner, A., et al., "Total Syntheses of the Phytotoxic Lactones Herbarumin I and II and a Synthesis–Based Solution of the Pinolidoxin Puzzle", J. Am. Chem. Soc. 2002, vol. 124, pp. 7061–7069.

Harrity, J.P.A., et al., "Chromenes through Metal–Catalyzed Reactions of Styrenyl Ethers. Mechanism and Utility in Synthesis", J. Am. Chem. Soc. 1998, vol. 120, pp. 2343–2351.

Harrity, J.P.A., et al., "Ru–Catalyzed Rearrangement of Styrenyl Ethers. Enantioselective Synthesis of Chromenes through Zr– and Ru–Catalyzed Processes", J. Am. Chem. Soc. 1997, vol. 119, pp. 1488–1489.

Miller, S.J., et al., "Catalytic Ring–Closing Metathesis of Dienes: Application to the Synthesis of Eight–Membered Rings", J. Am. Chem. Soc. 1995, vol. 117, pp. 2108–2109.

Piers, E., et al., "A new cycloheptenone annulation method: use of the bifunctional reagent (Z)–5–iodo–1–tributylstannylpent–1–ene in organic synthesis", J. Chem. Soc. Perkin Trans. vol. 1, 2000, pp. 635–637.

Ratcliffe, R. and Rodehorst, R., "Improved Procedure for Oxidations with the Chromium Trioxide–Pyridine Complex", J. Org. Chem., 1970, vol. 35, No. 11, pp. 4000–4002.

Scholl, M., et al., "Synthesis and Activity of a New Generation of Ruthenium–Based Olefin Metathesis Catalysts Coordinated with 1,3–Dimesityl–4, 5–dihydroimidazol–2–ylidene Ligands", Org. Lett. 1999, vol. 1, No. 6, pp. 953–956.

Schrock, R.R., et al., "Synthesis of Molybdenum Imido Alkylidene Complexes and Some Reactions Involving Acyclic Olefins", J. Am. Chem. Soc. 1990, vol. 112, pp. 3875–3886.

Schwab, P., et al., "A Series of Well–Defined Metathesis Catalysts —Synthesis of . . . ", Angew. Chem. Int. Ed. Engl. 1995, vol. 34, No. 18, pp. 2039–2041.

* cited by examiner

*Primary Examiner*—Bernard Dentz
(74) *Attorney, Agent, or Firm*—Nicole M. Beeler; Mark R. Daniel

(57) ABSTRACT

The present invention relates to processes for the synthesis of intermediates useful for the synthesis of estrogen receptor modulators. The process includes new methods for annelating 5-, 6- and 7-membered cycloalkenones onto an indanone.

21 Claims, No Drawings

PROCESS FOR THE SYNTHESIS OF ESTROGEN RECEPTOR MODULATORS

This application claims priority from Provisional Application No. 60/418,579 filed Oct. 15, 2002.

BACKGROUND OF THE INVENTION

Naturally occurring and synthetic estrogens have broad therapeutic utility, including: relief of menopausal symptoms, treatment of acne, treatment of dysmenorrhea and dysfunctional uterine bleeding, treatment of osteoporosis, treatment of hirsutism, treatment of prostatic cancer, treatment of hot flashes and prevention of cardiovascular disease. Because estrogen is very therapeutically valuable, there has been great interest in discovering compounds that mimic estrogen-like behavior in estrogen responsive tissues.

This invention relates to processes for making intermediates of estrogen receptor modulator compounds. The processes involve new methods for annelating 5-, 6- and 7-membered cycloalkenones onto an indanone.

SUMMARY OF THE INVENTION

The present invention relates to processes for the synthesis of compounds of formula I:

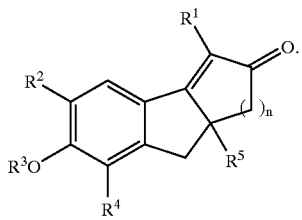

DETAILED DESCRIPTION OF THE INVENTION

The present invention relates to processes for the synthesis of compounds of formula I:

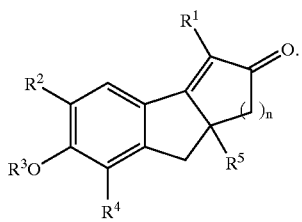

wherein $R^1$ is hydrogen, $C_{1-10}$alkyl, $C_{3-7}$cycloalkyl, (cycloalkyl)alkyl, aryl, heteroaryl, arylalkyl, (heteroaryl)alkyl or $SiR^aR^bR^c$ wherein said alkyl, cycloalkyl, aryl and heteroaryl groups are optionally substituted with 1, 2 or 3 groups selected from fluoro, chloro, bromo, iodo, $OR^d$, $NR^eR^f$, $O(C=O)NR^eR^f$, $NR^e(C=O)R^f$, $NR^e(C=O)OR^f$, $SR^e$, $S(O)R^e$, $SO_2R^e$, $SO_2NR^eR^f$, $LR^g$ or $MLR^g$;

$R^2$ is hydrogen, fluoro, chloro, bromo, iodo, methyl or $CF_3$;

$R^3$ is hydrogen, $C_{1-10}$alkyl, benzyl or a removable hydroxyl protecting group;

$R^4$ is hydrogen, fluoro, chloro, bromo, iodo, methyl or $CF_3$;

$R^5$ is hydrogen, $C_{1-10}$alkyl, $C_{2-10}$alkenyl, $C_{2-10}$alkynyl, $C_{3-6}$cycloalkyl, (cycloalkyl)alkyl, aryl, heteroaryl, arylalkyl or (hetereoaryl)alkyl wherein said alkyl, alkenyl, alkynyl, cycloalkyl, (cycloalkyl)alkyl, aryl, heteroaryl, arylalkyl and (heteroaryl)alkyl groups are optionally substituted with bromo, iodo, $OR^d$, $SR^e$, 1–3 $C_{1-3}$alkyl, 1–3 chloro or 1–5 fluoro;

$R^a$, $R^b$, and $R^c$ are independently selected from $C_{1-8}$alkyl, $O(C_{1-8}$alkyl) and phenyl;

$R_d$ is a removable hydroxyl protecting group, $C_{1-10}$alkyl, benzyl or phenyl, wherein said phenyl group is optionally substituted with 1–3 substituents independently selected from $C_{1-4}$alkyl, $O(C_{1-4}$alkyl), $NH(C_{1-4}$alkyl), $N(C_{1-4}$alkyl)$_2$ or halo;

$R^e$ is $C_{1-10}$alkyl or phenyl, wherein said alkyl group is optionally substituted with a group selected from $O(C_{1-4}$alkyl), $NH(C_{1-4}$alkyl), $N(C_{1-4}$alkyl)$_2$, phenyl or 1–5 fluoro, and wherein said phenyl group is optionally substituted with 1–3 substituents independently selected from $C_{1-4}$alkyl, $O(C_{1-4}$alkyl), $NH(C_{1-4}$alkyl), $N(C_{1-4}$alkyl)$_2$ or halo;

$R^f$ is $C_{1-10}$alkyl or phenyl, wherein said phenyl group is substituted with 1–3 substituents independently selected from $C_{1-4}$alkyl, $O(C_{1-4}$alkyl), $NH(C_{1-4}$alkyl), $N(C_{1-4}$alkyl)$_2$ or halo;

or $R^e$ and $R^f$, whether or not on the same atom, can be taken together with any attached and intervening atoms to form a 4–7 membered ring;

$R^g$ is $NR^eR^f$, $OR^d$, $NR^e(C=O)R^f$, $CONR^eR^f$, $SO_2NR^eR^f$ or a 4–9 membered mono- or bicyclic N-heterocycloalkyl ring that can be optonally substituted with 1–3 $C_{1-3}$alkyl and can be optionally interrupted by O, S or $NR^e$;

L is $CH_2$, $CR^eR^f$, or $C_{2-6}$alkylene, wherein said alkylene linker can be optionally interrupted by O, S or $NR^e$;

M is O, S, $NR^e$, $NR^e(C=O)$ or $(C=O)NR^e$;

and n is one, two or three.

The first step in the synthesis of compounds of formula I comprises alkylating of an indanone of formula II to yield an intermediate of formula III.

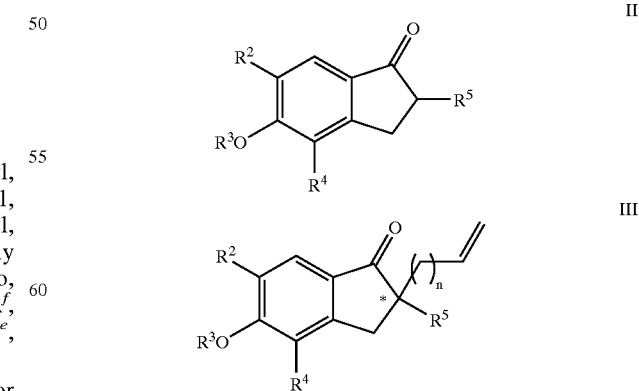

The alkylation is performed with an alkylating agent of formula VII in the presence of a base,

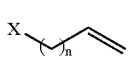  VII wherein X is Br, Cl, I, OMs, OTs or OTf, and n is as defined above. Suitable bases include, but are not limited to sodium hydride, potassium hydride, lithium diisopropylamide, lithium bis(trimethylsilyl)amide or sodium bis(trimethylsilyl)amide.

It is also possible to control the absolute stereochemistry of the chiral center which is generated in this alkylation reaction (indicated by an asterik in formula II). In this case, sodium or potassium hydroxide is used as a base in the presence of a chiral phase transfer catalyst. Suitable chiral phase transfer catalysts include, but are not limited to, N-benzylcinchoninium bromide, N-(p-trifluorobenzyl)cinchoninium bromide, N-(3,4-dichlorobenzyl)cinchoninium chloride, N-benzylcinchonidinium bromide, N-(p-trifluorobenzyl)cinchonidinium bromide or N-(3,4-dichlorobenzyl)cinchonidinium chloride.

Next, adding a nucleophile to an intermediate of formula III to yields a diene of formula IV.

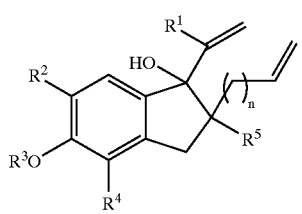  IV

The nucleophilic addition can be performed with an alkenyl metal species of formula VIII,

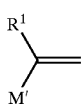  VIII wherein M' is MgBr, Li or Ce, and $R^1$ is as defined above.

The next step is cyclizing the compound of formula IV via a ring closing olefin metathesis reaction to yield an allylic alcohol of formula V.

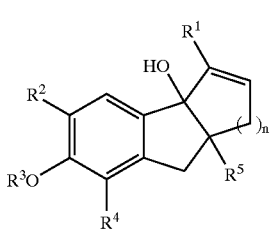  V

The ring closing olefin metathesis reaction is performed in the presence of a transition metal catalyst. Suitable transition metal catalysts include, but are not limited to:

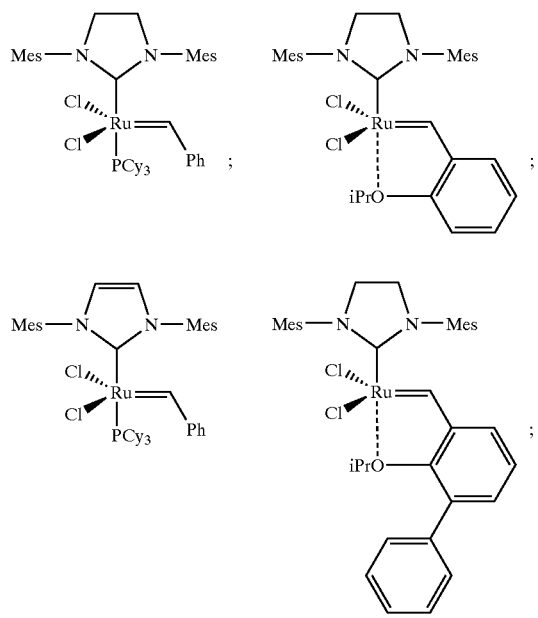

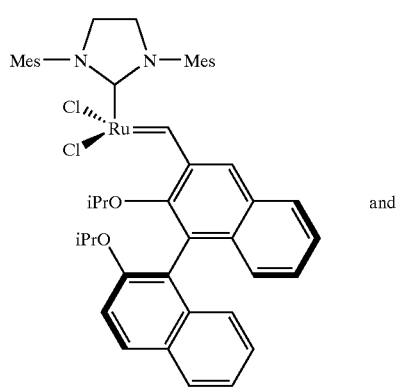

and

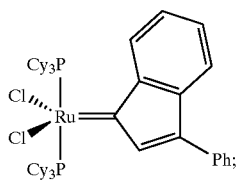

wherein

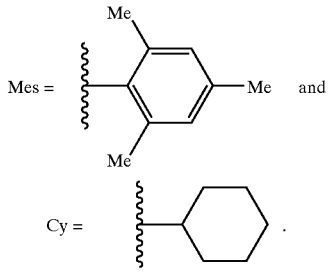

A preferred transition metal catalyst is

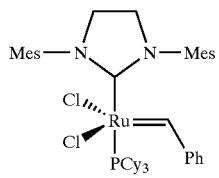

tricyclohexylphosphine[1,3-bis(2,4,6-trimethyl-phenyl)-4,5-dihydro-imidazol-2-ylidene]benzylidine ruthenium (IV) dichloride

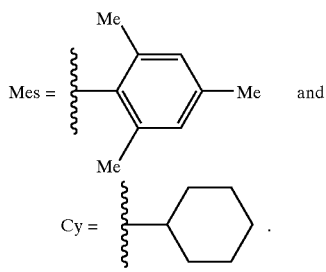

wherein

Other suitable catalysts for this ring closing olefin metathesis reaction are known in the art and are described in the following literature references [*Angew. Chem. Int. Ed.* 2002, 41, 794; *J. Am. Chem. Soc.* 2002, 124, 7061; *Angew. Chem. Int. Ed.* 2002, 41, 2403; *J. Am. Chem. Soc.* 2000, 122, 8168; *Org. Lett.* 2001, 3, 3225].

Alternatively, a chiral metathesis catalyst can be used during the ring closing olefin metathesis reaction. Suitable chiral metathesis catalysts include, but are not limited to:

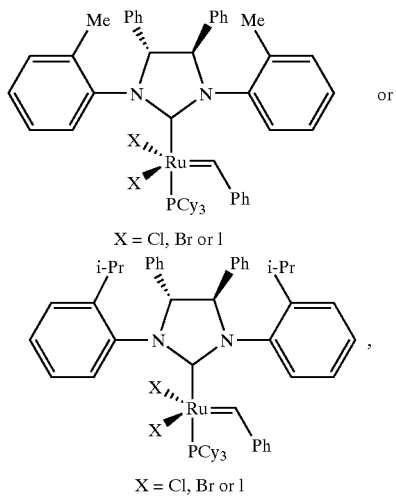

wherein

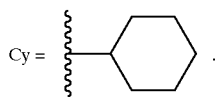

The following step comprises rearranging the compound of formula I via an allylic oxidative rearrangement to yield the enone of formula VI.

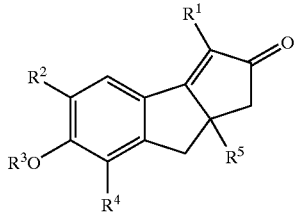

The allylic oxidative rearrangement is performed with a chromium (IV) oxidant. Suitable chromium (IV) oxidants include, but are not limited to, pyridinium chlorochromate, pyridinium dichromate, chromium trioxide and chromium trioxide-pyridine complex.

Depending on the $R^3$ chosen, the compound of formula VI may be equivalent to a compound of formula I. In the case where $R^3$ is hydrogen, final deprotection may be required to give a compound of formula I.

Another embodiment of the present invention relates to a process for the synthesis of estrogen receptor modulator compounds of formula IA:

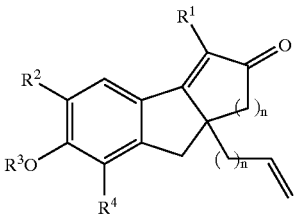

wherein $R^1$ is hydrogen, $C_{1-10}$alkyl, $C_{3-7}$cycloalkyl, (cycloalkyl)alkyl, aryl, heteroaryl, arylalkyl, (hetereoaryl)alkyl or $SiR^aR^bR^c$ wherein said alkyl, cycloalkyl, aryl and heteroaryl groups are optionally substituted with 1, 2 or 3 groups selected from fluoro, chloro, bromo, iodo, $OR^d$, $NR^eR^f$, $O(C=O)NR^eR^f$, $NR^e(C=O)R^f$, $NR^e(C=O)OR^f$, $SR^e$, $S(O)R^e$, $SO_2R^e$, $SO_2NR^eR^f$, $LR^g$ or $MLR^g$;

$R^2$ is hydrogen, fluoro, chloro, bromo, iodo, methyl or $CF_3$;

$R^3$ is hydrogen, $C_{1-10}$alkyl, benzyl or a removable hydroxyl protecting group;

$R^4$ is hydrogen, fluoro, chloro, bromo, iodo, methyl or $CF_3$;

$R^a$, $R^b$, and $R^c$ are independently selected from $C_{1-8}$alkyl, $O(C_{1-8}$alkyl) and phenyl;

$R_d$ is a removable hydroxyl protecting group, $C_{1-10}$alkyl, benzyl or phenyl, wherein said phenyl group is optionally substituted with 1–3 substituents independently selected from $C_{1-4}$alkyl, $O(C_{1-4}$alkyl), $NH(C_{1-4}$alkyl), $N(C_{1-4}$alkyl)$_2$ or halo;

$R^e$ is $C_{1-10}$alkyl or phenyl, wherein said alkyl group is optionally substituted with a group selected from $O(C_{1-4}$alkyl), $NH(C_{1-4}$alkyl), $N(C_{1-4}$alkyl)$_2$, phenyl or 1–5 fluoro, and wherein said phenyl group is optionally substituted with 1–3 substituents independently selected from $C_{1-4}$alkyl, $O(C_{1-4}$alkyl), $NH(C_{1-4}$alkyl), $N(C_{1-4}$alkyl)$_2$ or halo;

$R^f$ is $C_{1-10}$alkyl or phenyl, wherein said phenyl group is optionally substituted with 1–3 substituents independently selected from $C_{1-4}$alkyl, $O(C_{1-4}$alkyl), $NH(C_{1-4}$alkyl), $N(C_{1-4}$alkyl)$_2$ or halo;

or $R^e$ and $R^f$, whether or not on the same atom, can be taken together with any attached and intervening atoms to form a 4–7 membered ring;

$R^g$ is $NR^eR^f$, $OR^d$, $NR^e(C=O)R^f$, $CONR^eR^f$, $SO_2NR^eR^f$ or a 4–9 membered mono- or bicyclic N-heterocycloalkyl ring that can be optonally substituted with 1–3 $C_{1-3}$alkyl and can be optionally interrupted by O, S or $NR^e$;

L is $CH_2$, $CR^eR^f$, or $C_{2-6}$alkylene, wherein said alkylene linker can be optionally interrupted by O, S or $NR^e$;

M is O, S, $NR^e$, $NR^e(C=O)$ or $(C=O)NR^e$;

and n is one, two or three.

In the present invention, $R^e$ and $R^f$, whether or not on the same atom, can be taken together with any attached and intervening atoms to form a 4–7 membered ring. Said rings that can be formed include, but are not limited to, piperazinyl, pyridyl and pyrrolidinyl.

In the present invention, $R^g$ can be a 4–9 membered mono- or bicyclic N-heterocycloalkyl ring that can be optonally substituted with 1–3 $C_{1-3}$alkyl and can be optionally interrupted by O, S or $NR^e$. Nonlimiting examples of said rings include pyrrolidinyl, piperidinyl, piperazinyl and morpholino.

The first step in the synthesis of compounds of formula IA comprises alkylating an indanone of formula IIA to yield an intermediate of formula IIIA.

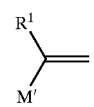

IIA

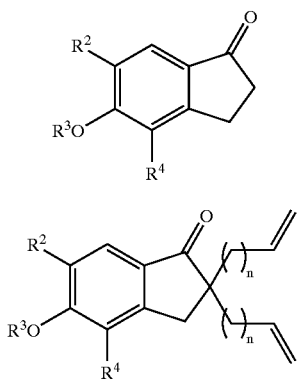

IIIA

The alkylation is performed with an alkylating agent of formula VII in the presence of a base,

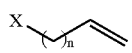

VII wherein X is Br, Cl, I, OMs, OTs or OTf, and n is as defined above.

Suitable bases for the alkylation include, but are not limited to, sodium hydride, potassium hydride, lithium diisopropylamide, lithium bis(trimethylsilyl)amide and sodium bis(trimethylsilyl)amide.

Next, adding a nucleophile to an intermediate of formula IIIA to yields a diene of formula IVA.

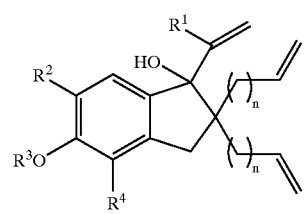

IVA

The nucleophilic addition can be performed with an alkenyl metal species of formula VIII,

VIII $$R^1 \atop M'$$

wherein M' is MgBr, Li or Ce, and $R^1$ is as defined above.

Next cyclizing the compound of formula IVA via a ring closing olefin metathesis reaction yields an allylic alcohol of formula VA.

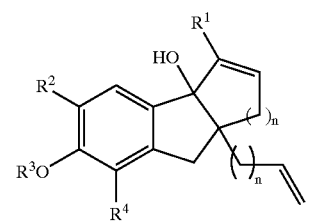

VA

The ring closing olefin metathesis reaction is performed in the presence of a transition metal catalyst. Suitable transition metal catalysts include, but are not limited to:

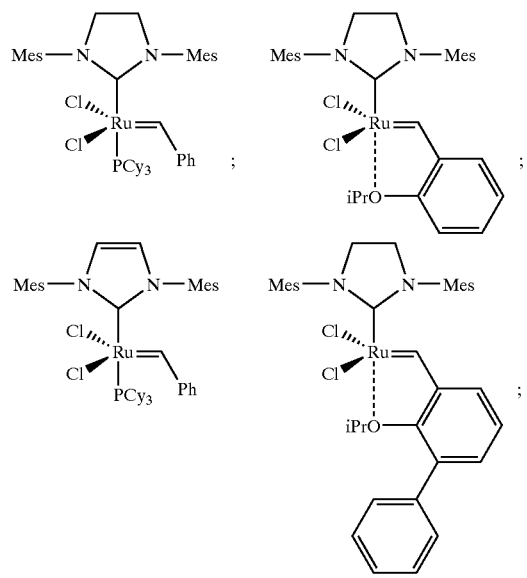

-continued

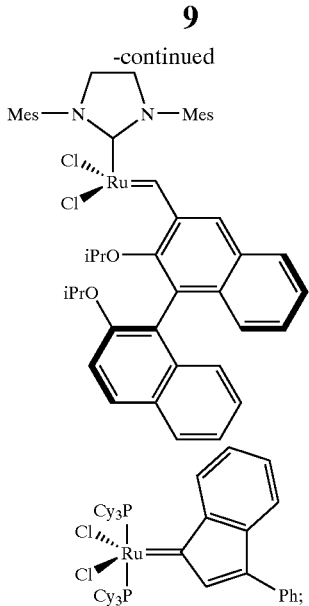

and wherein

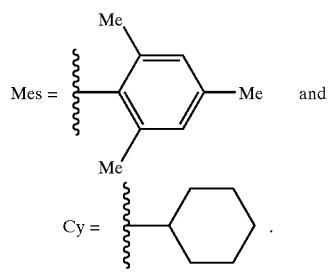

and

A preferred transition metal catalyst is

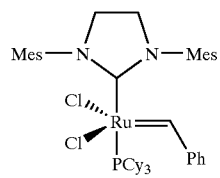

tricyclohexylphosphine[1,3-bis(2,4,6-trimethyl-phenyl)-4,5-dihydro-imidazol-2-ylidene]benzylidine ruthenium (IV) dichloride

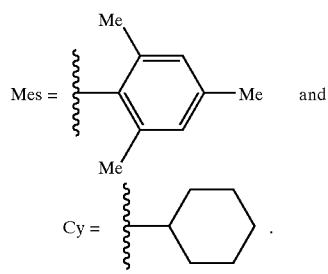

Other suitable catalysts for this ring closing olefin metathesis reaction are known in the art and are described in the following literature references [*Angew. Chem. Int. Ed.* 2002, 41, 794; *J. Am. Chem. Soc.* 2002, 124, 7061; *Angew. Chem. Int. Ed.* 2002, 41, 2403; *J. Am. Chem. Soc.* 2000, 122, 8168; *Org. Lett.* 2001, 3, 3225]. When n is 1 or 2, it is preferable to run this reaction in the presence of ethylene.

Alternatively, a chiral metathesis catalyst can be used during the ring closing olefin metathesis reaction. Suitable chiral metathesis catalysts include, but are not limited to:

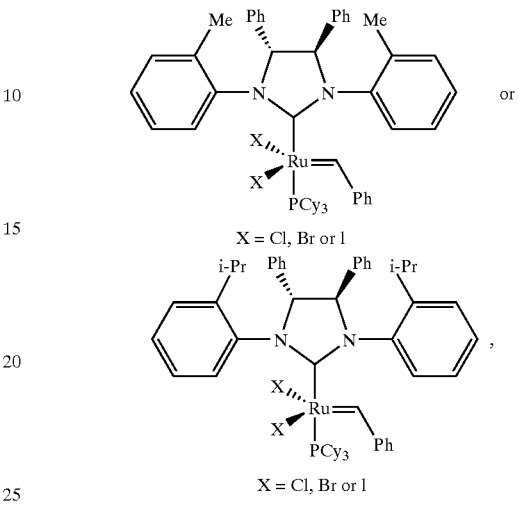

wherein

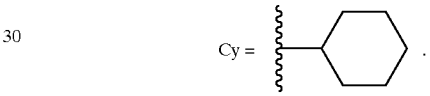

Next, rearranging the compound of formula V via an allylic oxidative rearrangement yields the enone of formula VIA.

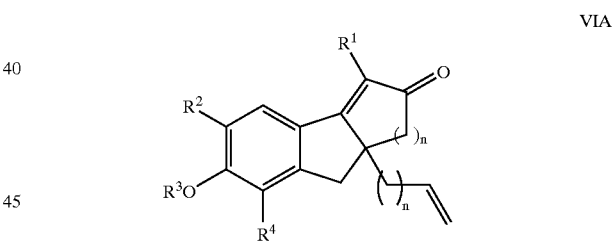

VIA

The allylic oxidative rearrangement is performed with a chromium (IV) oxidant. Suitable chromium (IV) oxidants include, but are not limited to, pyridinium chlorochromate, pyridinium dichromate, chromium trioxide and chromium trioxide-pyridine complex.

Depending on the $R^3$ chosen, the compound of formula VIA may be equivalent to a compound of formula IA. In the case where $R^3$ is hydrogen, final deprotection may be required to give a compound of formula IA.

Definitions

The term "alkyl" shall mean a substituting univalent group derived by conceptual removal of one hydrogen atom from a straight or branched-chain acyclic saturated hydrocarbon (i.e., $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-C(CH_3)_3$, etc.).

The term "alkenyl" shall mean a substituting univalent group derived by conceptual removal of one hydrogen atom from a straight or branched-chain acyclic unsaturated hydrocarbon containing at least one double bond (i.e., —CH=CH$_2$, —CH$_2$CH=CH$_2$, —CH=CHCH$_3$, —CH$_2$CH=C(CH$_3$)$_2$, etc.).

The term "alkynyl" shall mean a substituting univalent group derived by conceptual removal of one hydrogen atom from a straight or branched-chain acyclic unsaturated hydrocarbon containing at least one triple bond (i.e., —C≡CH, —CH$_2$C≡CH, —C≡CCH$_3$, —CH$_2$C≡CCH$_2$(CH$_3$)$_2$, etc.).

The term "alkylene" shall mean a substituting bivalent group derived from a straight or branched-chain acyclic saturated hydrocarbon by conceptual removal of two hydrogen atoms from different carbon atoms (i.e., —CH$_2$CH$_2$—, —CH$_2$CH$_2$CH$_2$CH$_2$—, —CH$_2$C(CH$_3$)$_2$CH$_2$—, etc.).

The term "cycloalkyl" shall mean a substituting univalent group derived by conceptual removal of one hydrogen atom from a saturated monocyclic hydrocarbon (i.e., cyclopropyl, cyclobutyl, cyclopentyl, cyclohexyl, or cycloheptyl).

The term "heterocycloalkyl" shall mean a substituting univalent group derived by conceptual removal of one hydrogen atom from a heterocycloalkane wherein said heterocycloalkane is derived from the corresponding saturated monocyclic hydrocarbon by replacing one or two carbon atoms with atoms selected from N, O or S. Examples of heterocycloalkyl groups include, but are not limited to, oxiranyl, azetidinyl, pyrrolidinyl, piperidinyl, piperazinyl, and morpholinyl. Heterocycloalkyl substituents can be attached at a carbon atom. If the substituent is a nitrogen containing heterocycloalkyl substituent, it can be attached at the nitrogen atom.

The term "aryl" as used herein refers to a substituting univalent group derived by conceptual removal of one hydrogen atom from a monocyclic or bicyclic aromatic hydrocarbon. Examples of aryl groups are phenyl, indenyl, and naphthyl.

The term "heteroaryl" as used herein refers to a substituting univalent group derived by the conceptual removal of one hydrogen atom from a monocyclic or bicyclic aromatic ring system containing 1, 2, 3, or 4 heteroatoms selected from N, O, or S. Examples of heteroaryl groups include, but are not limited to, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl, and purinyl. Heteraryl substituents can be attached at a carbon atom or through the heteroatom.

In the compounds of the present invention, alkyl, alkenyl, alkynyl, alkylidene, alkenylene, cycloalkyl, cycloalkyl, heterocycloalkyl, aryl and heteroaryl groups can be further substituted by replacing one or more hydrogen atoms by alternative non-hydrogen groups. These include, but are not limited to, halo, hydroxy, mercapto, amino, carboxy, cyano, carbamoyl, and oxo.

Whenever the term "alkyl" or "aryl" or either of their prefix roots appear in a name of a substituent (e.g., aryl C$_{1-8}$alkyl) it shall be interpreted as including those limitations given above for "alkyl" and "aryl." Designated numbers of carbon atoms (e.g., C$_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, and chlorophenylethyl. Examples of alkylaryl include, but are not limited to, toluyl, ethylphenyl, and propylphenyl.

The term "(heteroaryl)alkyl," as used herein, shall refer to a system that includes a heteroaryl portion, where heteroaryl is as defined above, and contains an alkyl portion. Examples of (heteroaryl)alkyl include, but are not limited to, thienylmethyl, thienylethyl, thienylpropyl, pyridylmethyl, pyridylethyl and imidazoylmethyl.

The term "(cycloalkyl)alkyl," as used herein, shall refer to a system that includes a 3- to 7-membered fully saturated cyclic ring portion and also includes an alkyl portion, wherein cycloalkyl and alkyl are as defined above.

The term "halo" shall include iodo, bromo, chloro and fluoro.

The term "oxy" means an oxygen (O) atom. The term "thio" means a sulfur (S) atom. The term "oxo" means =O. The term "oximino" means the =N—O group.

The term "removable hydroxyl protecting group" refers to groups which are used to protectively block the hydroxyl group during the synthesis procedures of the current invention. These conventional protecting groups are removable, i.e. they can be removed if desired by procedures which will not cause cleavage or other disruption of the remaining portions of the molecule. Suitable removable hydroxyl protecting groups include the following: methoxymethyl, benzyloxymethyl, 2-(trimethylsilyl)ethoxymethyl, tetrahydropyranyl, p-methoxybenzyl, 3,4-dimethoxybenzyl, diphenylmethyl, triphenylmethyl. t-butyldimethylsilyl, and t-butyldiphenylsilyl. A comprehensive list of suitable protective groups can be found in T. W. Greene and P. G. M. Wuts, *Protective Groups in Organic Synthesis*, John Wiley & Sons, Inc. 1999, the disclosure of which is incorporated herein by reference in its entirety.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The alkyl, alkenyl, alkynyl, cycloalkyl, cycloalkenyl, aryl, heterocycloalkyl and heteroaryl substituents may be unsubstituted or unsubstituted, unless specifically defined otherwise. For example, a C$_{1-10}$alkyl may be substituted with one or more substituents selected from hydroxy, oxo, halogen, alkoxy, dialkylamino, or carboxy, and so on. In the case of a disubstituted alkyl, for instance, wherein the substituents are oxo and OH, the following are included in the definition: —(C=O)CH$_2$CH(OH)CH$_3$, —(C=O)OH, —CH$_2$(OH)CH$_2$CH(O), and so on. In the case of substituted alkyl, for instance, where the substituents are 1–5 fluoro, the following are included in the definition: —CHF$_2$, —CF$_3$, —CF$_2$CH$_3$, —CH$_2$CF$_3$, —CF$_2$CF$_3$, —CH$_2$CF$_2$CH$_3$, —CH$_2$CH$_2$CF$_3$, —CH$_2$CF$_2$CF$_3$, —CH$_2$CF$_2$CH$_2$CH$_3$, —CH$_2$CH$_2$CF$_2$CH$_3$, —CH$_2$CH$_2$CF$_2$CF$_3$, —CH$_2$CF(CH$_3$)$_2$, and so on. In the case cycloalkylalkyl group, for instance, wherein the substituents are 1–3 C$_{1-3}$alkyl, the following are included in the definition:

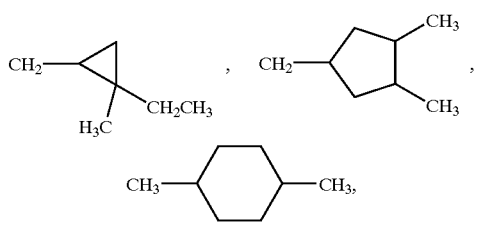

an so on

When any variable (e.g. $R^a$, $R^b$, $R^c$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the sub-stitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

Under standard nonmenclature used throughout this disclosure, the terminal portion of the designated side chain is described first, followed by the adjacent functionality toward the point of attachment. For example, a $C_{1-5}$ alkyl-carbonylamino $C_{1-6}$alkyl substituent is equivalent to

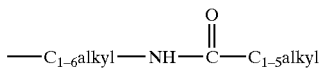

In choosing compounds of the present invention, one of ordinary skill in the art will recognize that the various substituents, i.e. $R^1$, $R^2$ and $R^3$ are to be chosen in conformity with well-known principles of chemical structure connectivity.

The following specific examples are not intended to limit the present invention, but to illustrate aspects of the present invention. Those skilled in the art will readily understand that known variations of the conditions and processes of the following preparative procedures can be used to prepare these compounds. All temperatures are degrees Celsius unless otherwise noted.

EXAMPLE 1

Synthesis of 8a-allyl-6-methoxy-3-methyl-8,8a-dihydrocyclopenta[a]inden-2(1H)-one

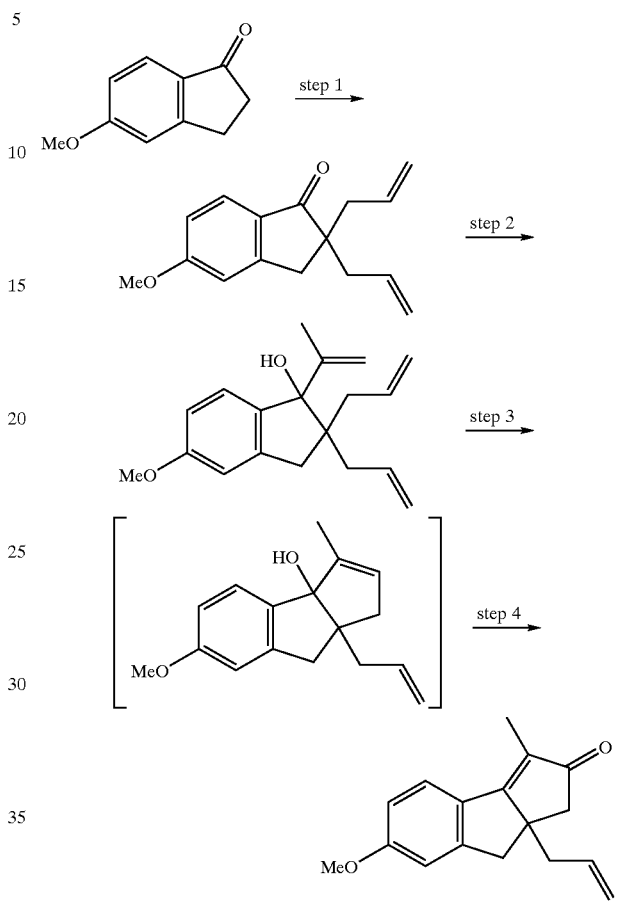

Step 1: 2,2-diallyl-5-methoxy-1-indanone

To a solution of 5-methoxy-1-indanone (324 mg, 2 mmol) in DMF (10 mL) at 0° C. was added NaH (160 mg, 61% in oil, 4 mmol) and allyl bromide (0.38 mL, 4 mmol). After 2 h at rt, another portion of NaH (32 mg) and allyl bromide (0.06 mL) was introduced. After about another 30 min, the solution was diluted with EtOAc and washed with water twice. The EtOAc layer was dried with $MgSO_4$ and filtered through a plug of silica. The filtrate was concentrated and provided crude 2,2-diallyl-5-methoxy-1-indanone.

Step 2: 2,2-diallyl-1-isopropenyl-5-methoxy-1-indanone

To neat 2,2-diallyl-5-methoxy-1-indanone (~2 mmol) was added isopropenyl magnesium bromide (20 mL, 0.5 M in THF, 10 mmol). After stirring at rt overnight, the solution was diluted with EtOAc and washed with water twice. The EtOAc layer was dried with $Na_2SO_4$ and filtered through a plug of silica. The filtrate was concentrated and provided crude 2,2-diallyl-1-isopropenyl-5-methoxy-1-indanone.

Steps 3 and 4: 8a-allyl-6-methoxy-3-methyl-8,8a-dihydrocyclopenta[a]inden-2(1H)-one To a solution of 2,2diallyl-1-isopropenyl-5-methoxy-1-indanone (~0.2 mmol; 10% of the crude product prepared in Step 2) in $CH_2Cl_2$ (40 mL) at −78° C. was added tricyclohexylphosphine[1,3-bis(2,4,6-trimethyl-phenyl)-4,5-dihydro-imidazol-2-ylidene]benzylidine ruthenium(IV) dichloride (32 mg, ~0.04 mmol). Ethylene gas in a balloon was charged through 3 repetitions of a vacuum/ethylene sequence. The solution was stirred at room temperature overnight. At timepoints of 1 h and 15 h, 1 mL aliquots were syringed out for NMR evaluation and not added back. After about 16 h, PDC (150 mg, 0.4 mmol) was added and the reaction mixture was stirred for 4 h. The solution was diluted with Et$_2$O (50 mL) and filtered through a plug of silica. The filtrate was concentrated and purified by PLC which provided 8a-allyl-6-methoxy-3-methyl-8,8a-dihydrocyclopenta[a]inden-2(1H)-one.

$^1$H NMR (CDCl$_3$, 500 MHz) δ 1.93 (s, 3-CH$_3$), 2.08 and 2.26 (two m, CH$_2$CHCH$_2$), 2.46 and 2.60 (two d, 1-CH$_2$), 2.82 and 3.00 (two d, 8-CH$_2$), 3.86 (s, O—CH$_3$), 5.00 (m, CH$_2$CHCH$_2$), 5.65 (m, CH$_2$CHCH$_2$), 6.88 (d, H-5), 6.90 (s, H-7), and 7.56 (d, H-4).

EXAMPLE 2

Synthesis of 9a-(3-butenyl)-7-methoxy-4-methyl-1,2,9,9a-tetrahydro-3H-fluoren-3-one

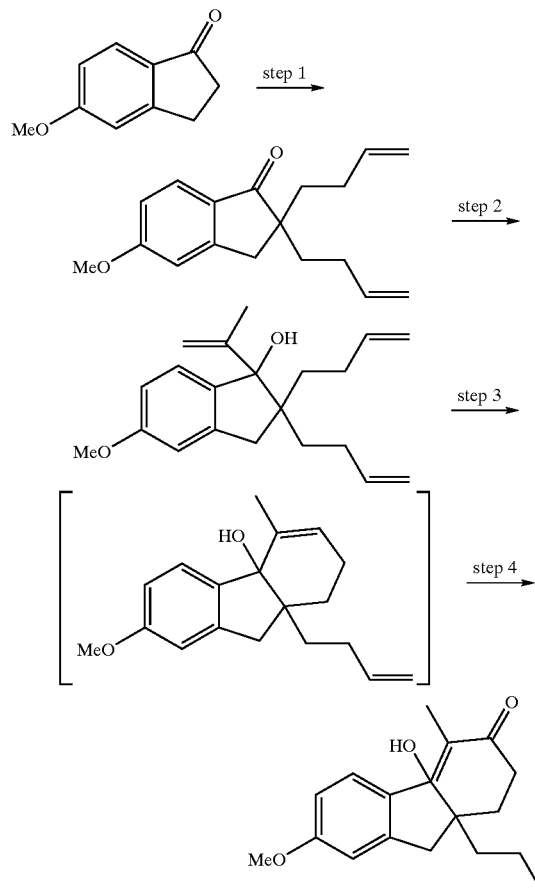

Step 1: 2,2-di(3-butenyl)-5-methoxy-1-indanone

To a solution of 5-methoxy-1-indanone (1 g, 6.17 mmol) in DMF (6 mL) at rt was added NaH (740 mg, 61% in oil, 18.5 mmol) and 4-bromo-1-butene (2.5 mL, 24.7 mmol). After 20 h at rt, the solution was diluted with CH$_2$Cl$_2$ and quenched with saturated aqueous NH$_4$Cl. The slurry was dried with MgSO$_4$ and filtered through a plug of silica and rinsed with 10% EtOAc in hexanes. The filtrate was concentrated and provided crude 2,2-di(3-butenyl)-5-methoxy-1-indanone.

Step 2: 2,2-di(3-butenyl)-1-isopropenyl-5-methoxy-1-indanone

To neat 2,2-di(3-butenyl)-5-methoxy-1-indanone (90% of the crude product from Step 1, ~5.56 mmol) was added isopropenyl magnesium bromide (56 mL, 0.5 M in THF, 27.8 mmol). After stirring at rt overnight, the solution was diluted with EtOAc and washed with water twice. The EtOAc layer was dried with Na$_2$SO$_4$ and filtered through a plug of silica. The filtrate was concentrated to provide crude 2,2-di(3-butenyl)-1-isopropenyl-5-methoxy-1-indanone.

Steps 3 and 4: 9a-di(3-butenyl)-7-methoxy-4-methyl-1,2,9,9a-tetrahydro-3H-fluoren-3-one To a solution of 2,2-di(3-butenyl)-1-isopropenyl-5-methoxy-1-indanone (~0.1 mmol) in CH$_2$Cl$_2$ (20 mL) at −78° C. was added tricyclohexylphosphine[1,3-bis(2,4,6-trimethyl-phenyl)-4,5-dihydro-imidazol-2-ylidene]benzylidine ruthenium(IV) dichloride (8.5 mg, ~0.01 mmol). Ethylene gas in a balloon was charged through 3 repetitions of a vacuum/ethylene sequence. After the solution was stirred at room temperature overnight, an additional 17 mg of the above ruthenium catalyst in CH$_2$Cl$_2$ (1 mL) was injected into the reaction system. At timepoints of 2, 12 and 36 h, 1 mL aliquots were syringed out for NMR evaluation and not added back. After about 40 h, PDC (70 mg, 0.2 mmol) was added and the reaction mixture was stirred for 2 h. The solution was diluted with Et$_2$O (50 mL) and filtered through a plug of silica. The filtrate was concentrated and purified by PLC providing 9a-(3-butenyl)-7-methoxy-4-methyl-1,2,9,9a-tetrahydro-3H-fluoren-3-one.

$^1$H NMR (CDCl$_3$, 500 MHz) δ 1.56 (m, 1H), 1.62 (m, 1H), 1.72 (m, 1H), 2.02 (m, 2H), 2.08 (s, 3H), 2.23 (m, 1H), 2.48 (m, 1H), 2.58 (m, 1H), 2.76 and 2.98 (two d), 3.86 (s, O—CH$_3$), 4.92 (m, 2H), 5.70 (m, 1H), 6.86 (m, 2H) and 7.64 (d, 1H).

EXAMPLE 3

Synthesis of 2-methoxy-5-methyl-9a-(4-pentenyl)-8,9,9a,10-tetrahydrobenzo[a]azulen-6(7H)-one

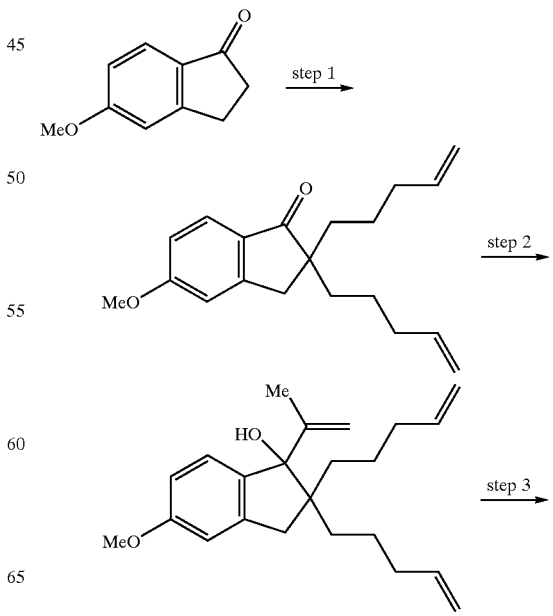

EXAMPLE 4

Synthesis of 9a-butyl-2-hydroxy-5-methyl-8,9,9a,10-tetrahydrobenzo[a]azulen-6(7H)-one

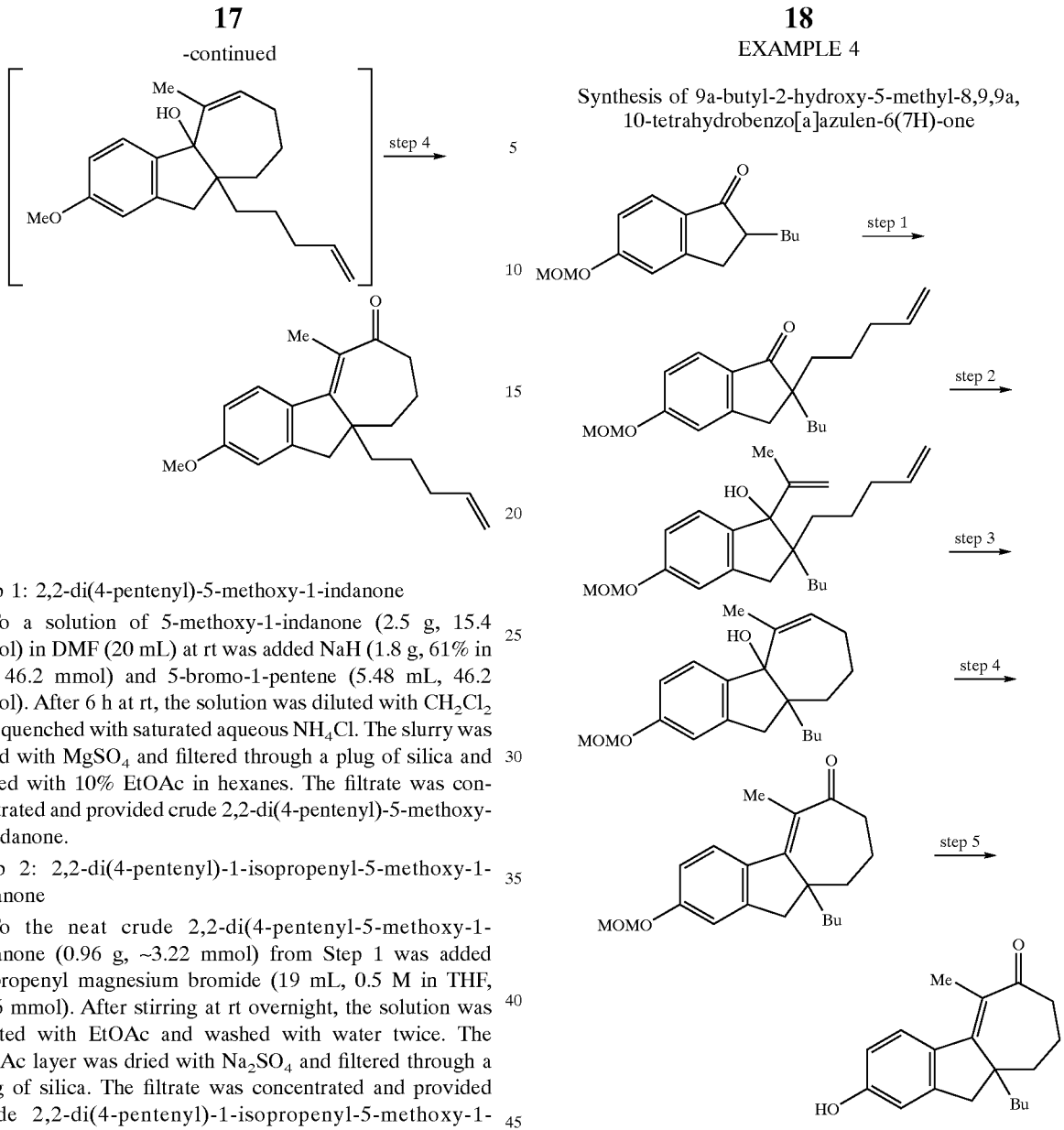

Step 1: 2,2-di(4-pentenyl)-5-methoxy-1-indanone

To a solution of 5-methoxy-1-indanone (2.5 g, 15.4 mmol) in DMF (20 mL) at rt was added NaH (1.8 g, 61% in oil, 46.2 mmol) and 5-bromo-1-pentene (5.48 mL, 46.2 mmol). After 6 h at rt, the solution was diluted with $CH_2Cl_2$ and quenched with saturated aqueous $NH_4Cl$. The slurry was dried with $MgSO_4$ and filtered through a plug of silica and rinsed with 10% EtOAc in hexanes. The filtrate was concentrated and provided crude 2,2-di(4-pentenyl)-5-methoxy-1-indanone.

Step 2: 2,2-di(4-pentenyl)-1-isopropenyl-5-methoxy-1-indanone

To the neat crude 2,2-di(4-pentenyl)-5-methoxy-1-indanone (0.96 g, ~3.22 mmol) from Step 1 was added isopropenyl magnesium bromide (19 mL, 0.5 M in THF, 9.66 mmol). After stirring at rt overnight, the solution was diluted with EtOAc and washed with water twice. The EtOAc layer was dried with $Na_2SO_4$ and filtered through a plug of silica. The filtrate was concentrated and provided crude 2,2-di(4-pentenyl)-1-isopropenyl-5-methoxy-1-indanone.

Steps 3 and 4: 2-methoxy-5-methyl-9a-(4-pentenyl)-8,9,9a,10-tetrahydrobenzo[a]azulen-6(7H)-one To a solution of 2,2-di(4-pentenyl)-1-isopropenyl-5-methoxy-1-indanone (~0.1 mmol) in $CH_2Cl_2$ (20 mL) at room temperature was added tricyclohexylphosphine[1,3-bis(2,4,6-trimethyl-phenyl)-4,5-dihydro-imidazol-2-ylidene]benzylidine ruthenium(IV) dichloride (17 mg, ~0.02 mmol). After the solution was stirred at 40° C. for 2 h, freshly prepared Ratcliffe reagent [$CrO_3$ (180 mg, 1.8 mmol), pyridine (0.32 mL, 4.0 mmol) and $CH_2Cl_2$ (2 mL)] was added and the reaction mixture was stirred for 2 h. The solution was diluted with $Et_2O$ (50 mL) and filtered through a plug of silica. The filtrate was concentrated and purified by PLC, which provided 2-methoxy-5-methyl-9a-(4-pentenyl)-8,9,9a,10-tetrahydrobenzo[a]azulen-6(7H)-one.

$^1$H NMR (CDCl$_3$, 500 MHz) δ 1.36 (m, 2H), 1.48 (m, 1H), 1.58 (m, 2H), 1.95 (m, 5H), 2.16 (s, 3H), 2.63 (m, 1H), 2.83 (m, 1H), 2.79 and 2.93 (two d), 3.83 (s, O—CH$_3$), 4.90 (m, 2H), 5.70 (m, 1H), 6.79 (m, 2H) and 7.54 (d, 1H).

Step 1: 2-butyl-5-(methoxymethoxy)-2-(4-pentenyl)-1-indanone

A solution of 2-butyl-5-(methoxymethoxy)-1-indanone (1.54 g, 6.2 mmol) in anhydrous N,N-dimethylformamide (DMF, 5 mL) was added to a suspension of sodium hydride (372 mg of a 60% dispersion in mineral oil, 9.3 mmol) in DMF (5 mL). The mixture was diluted with more DMF (2 mL, used to rinse in the indanone solution), placed under a nitrogen atmosphere, and stirred at room temperature for 25 minutes. 5-Bromo-1-pentene (1.47 mL, 12.4 mmol) was then added over 5 minutes, during which time the mixture clarified. After stirring at room temperature for an additional 5 hours, the mixture was quenched with saturated $NH_4Cl$, dried over $MgSO_4$, filtered through a pad of silica, and concentrated under vacuum to afford an oil. The crude product was purified by Biotage™ (Charlottesville, Va.) flash chromatography on a 40S (4.0×7.0 cm) silica gel column, eluting with 19:1 hexanes-EtOAc. The product-containing fractions were evaporated under vacuum to afford 2-butyl-5-(methoxymethoxy)-2-(4-pentenyl)-1-indanone as an oil.

Step 2: 2-butyl-1-isopropenyl-5-(methoxymethoxy)-2-(4-pentenyl)-1-indanol

A solution of 2-butyl-5-(methoxymethoxy)-2-(4-pentenyl)-1-indanone (400 mg, 1.27 mmol) in anhydrous tetrahydrofuran (THF, 5 mL) was placed under a $N_2$ atmosphere, cooled in a dry ice-acetone bath, stirred, and treated with 2-propenyl magnesium bromide, (1M in THF, 1.9 mL, 1.9 mmol). After warming to room temperature, the mixture was treated with additional 2-propenyl magnesium bromide (1M in THF, 6 mL, 6 mmol) and stirred at room temperature overnight. The mixture was quenched with saturated aqueous $NH_4Cl$, dried over $MgSO_4$, filtered through a pad of silica, and concentrated under vacuum to afford an oil. The crude product was purified by Biotage™ (Charlottesville, Va.) flash chromatography on a 40S (4.0× 7.0 cm) silica gel column, eluting with 19:1 hexanes-EtOAc. The product-containing fractions were evaporated under vacuum to afford 2-butyl-1-isopropenyl-5-(methoxymethoxy)-2-(4-pentenyl)-1-indanol as an oil.

Step 3: 9a-butyl-2-(methoxymethoxy)-5-methyl-8,9,9a,10-tetrahydrobenzo[a]azulen-4b(7H)-ol A solution of 2-butyl-1-isopropenyl-5-(methoxymethoxy)-2-(4-pentenyl)-1-indanol (200 mg, 0.56 mmol) in dichloromethane (22 mL) was treated with tricyclohexylphosphine[1,3-bis(2,4,6-trimethylphenyl)-4,5-dihydro-imidazol-2-ylidene]benzylidine ruthenium(IV) dichloride (47 mg, 0.056 mmol). After stirring at 45° C. overnight, the mixture was treated with additional tricyclohexylphosphine[1,3-bis(2,4,6-trimethylphenyl)-4,5-dihydro-imidazol-2-ylidene]benzylidine ruthenium (IV) dichloride (47 mg, 0.056 mmol) and stirred at 45° C. for another 24 hours. The mixture was concentrated and the residue purified by preparative layer chromatography on two 0.1×20×20 cm silica gel GF plates (Analtech, Newark, Del.), developing with 10% EtOAc in hexane. The UV visible product band was eluted with EtOAc and the eluant was evaporated under vacuum to provide 9a-butyl-2-(methoxymethoxy)-5-methyl-8,9,9a,10-tetrahydrobenzo[a]azulen-4b(7H)-ol as an oil.

Step 4: 9a-butyl-2-(methoxymethoxy)-5-methyl-8,9,9a,10-tetrahydrobenzo[a]azulen-6(7H)-one A solution of 9a-butyl-2-(methoxymethoxy)-5-methyl-8,9,9a,10-tetrahydrobenzo[a]azulen-4b(7H)-ol (32 mg, 0.1 mmol) in dichloromethane (1 mL) was treated with pyridinium chlorochromate (PCC, 32 mg, 0.15 mmol). After stirring at room temperature for 5 hours, the mixture was treated with additional PCC (5 mg, 0.023 mmol). The mixture was concentrated and purified by preparative layer chromatography on a 0.1×20×20 cm silica gel GF plate (Analtech, Newark, Del.), developing with 10% EtOAc in hexane. The UV visible product band was eluted with EtOAc and the eluant was evaporated under vacuum to provide 9a-butyl-2-(methoxymethoxy)-5-methyl-8,9,9a,10-tetrahydrobenzo[a]azulen-6(7H)-one as an oil.

Step 5: 9a-butyl-2-hydroxy-5-methyl-8,9,9a,10-tetrahydrobenzo[a]azulen-6(7H)-one A solution of 9a-butyl-2-(methoxymethoxy)-5-methyl-8,9,9a,10-tetrahydrobenzo[a]azulen-6(7H)-one(5 mg) in methanol (1 mL) was treated with aqueous 2N HCl (0.1 mL, 0.2 mmol). After stirring at 65° C. for two hours, the mixture was diluted with dichloromethane(2 mL), treated with solid $NaHCO_3$, and purified by preparative layer chromatography on a 0.1×20×20 cm silica gel GF plate (Analtech, Newark, Del.), developing with 20% EtOAc in hexane. The UV visible product band was eluted with EtOAc and the eluant was evaporated under vacuum to provide 9a-butyl-2-hydroxy-5-methyl-8,9,9a,10-tetrahydrobenzo[a]azulen-6(7H)-one as a foam.

$^1$H NMR (CDCl$_3$, 500 MHz) δ 0.82 (t, CH$_2$CH$_2$CH$_2$CH$_3$), 1.10–1.23 (m, CH$_2$CH$_2$CH$_2$CH$_3$), 1.44 and 1.56 (two m, CH$_2$CH$_2$CH$_2$CH$_3$), 1.84–2.02 (m, 8-CH$_2$ and 9-CH$_2$), 2.16 (s, 5-CH$_3$), 2.63 and 2.84 (two ddd, 7-CH$_2$), 2.74 and 2.91 (two d, 10-CH$_2$), 5.11 (s, OH), 6.72 (m, H-1 and H-3), and 7.49 (d, H-4); mass spectrum m/z 285.3 (M+1).

EXAMPLE 5

Synthesis of 9a-butyl-7-methoxy-4-methyl-1,2,9,9a-tetrahydro-3H-fluoren-3-one

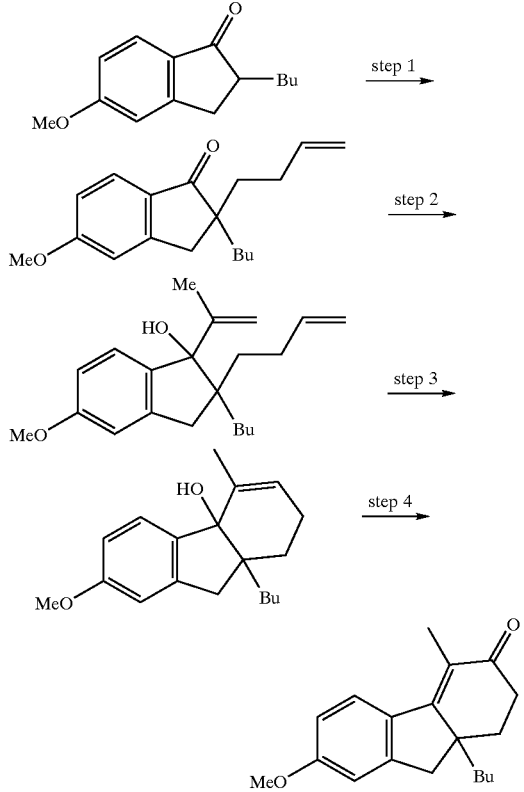

Employing procedures analogous to those described in Example 4, but starting with 2-butyl-5-methoxy-1-indanone and utilizing 4-bromo-1-butene in place of 5-bromo-1-pentene in Step 1, the title compound was prepared.

$^1$H NMR (CDCl$_3$, 500 MHz) δ 0.82 (t, CH$_2$CH$_2$CH$_2$CH$_3$), 1.16–1.26 (m, CH$_2$CH$_2$CH$_2$CH$_3$), 1.36 and 1.58 (two m, CH$_2$CH$_2$CH$_2$CH$_3$), 1.96 and 2.22 (m, 1-CH$_2$), 2.07 (s, 5-CH$_3$), 2.46 and 2.57 (two ddd, 2-CH$_2$), 2.70 and 2.96 (two d, 9-CH$_2$), 3.85 (s, O—CH$_3$), 6.85 (m, H-6 and H-8), and 7.49 (d, H-5).

EXAMPLE 6

Synthesis of 8a-propyl-6-methoxy-3-methyl-8,8a-dihydrocyclopenta[a]inden-2(1H)-one

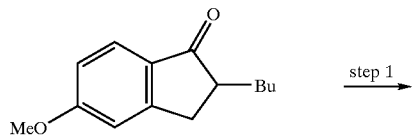

-continued

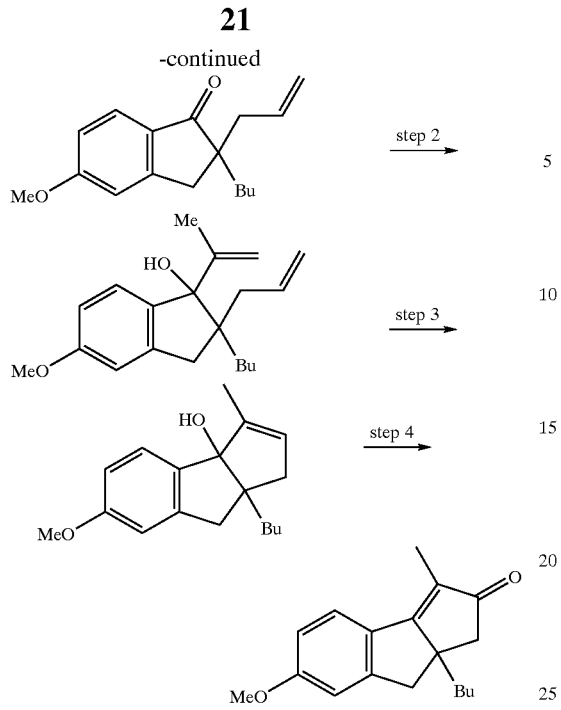

Employing procedures analogous to those described in Example 4, but starting with 2-butyl-5-methoxy-1-indanone and utilizing allyl bromide in place of 5-bromo-1-pentene in Step 1, the title compound was prepared.

$^1$H NMR (CDCl$_3$, 500 MHz) δ 0.80 (t, CH$_2$CH$_2$CH$_2$CH$_3$), 1.06–1.20 (m, CH$_2$CH$_2$CH$_2$CH$_3$), 1.35 and 1.58 (two m, CH$_2$CH$_2$CH$_2$CH$_3$), 1.93 (s, 3-CH$_3$), 2.46 and 2.56 (two d, 1-CH$_2$), 2.82 and 2.96 (two d, 8-CH$_2$), 3.84 (s, O—CH$_3$), 6.86 (d, H-5), 6.88 (s, H-7), and 7.55 (d, H-4).

What is claimed is:

1. A process for making compounds of formula I:

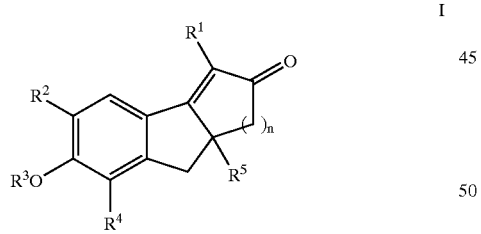

comprising the steps of:

a. alkylating an indanone of formula II to yield an intermediate of formula III;

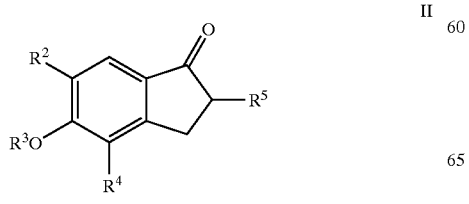

-continued

b. adding a nucleophile to the intermediate of formula III to yield a diene of formula IV;

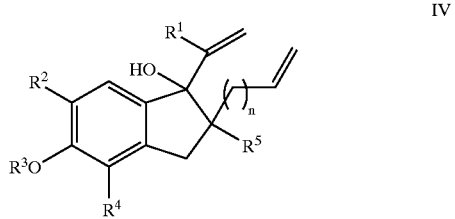

c. cyclizing the diene of formula IV via a ring closing olefin metathesis reaction to yield an allylic alcohol of formula V;

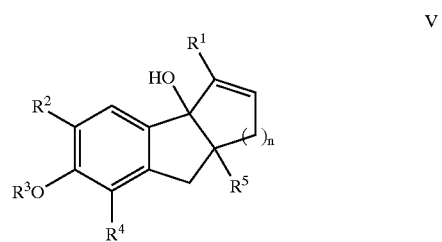

d. rearranging the compound of formula V via an allylic oxidative rearrangement to yield an en one of formula VI;

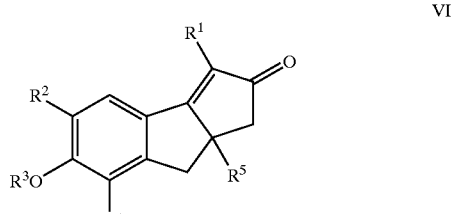

e. optionally deprotecting R$^3$;

wherein R$^1$ is hydrogen, C$_{1-10}$ alkyl, C$_{3-7}$ cycloalkyl, (cycloalkyl)alkyl, aryl, heteroaryl, arylalkyl, (heteroaryl)alkyl or SiR$^a$R$^b$R$^c$ wherein said alkyl, cycloalkyl, aryl and heteroaryl groups are optionally substituted with 1, 2 or 3 groups selected from fluoro, chloro, bromo, iodo, OR$^d$, NR$^e$R$^f$, O(C=O)NR$^e$R$^f$, NR$^e$(C=O)R$^f$, NR$^e$(C=O)OR$^f$, SR$^e$, S(O)R$^e$, SO$_2$R$^e$, SO$_2$NR$^e$R$^f$, LR$^g$ or MLR$^g$;

R$^2$ is hydrogen, fluoro, chloro, bromo, iodo, methyl or CF$_3$;

R$^3$ is hydrogen, C$_{1-10}$ alkyl, benzyl or a removable hydroxyl protecting group;

R$^4$ is hydrogen, fluoro, chloro, bromo, iodo, methyl or CF$_3$;

$R^5$ is hydrogen, $C_{1-10}$ alkyl, $C_{2-10}$ alkenyl, $C_{2-10}$ alkynyl, $C_{3-6}$ cycloalkyl, (cycloalkyl)alkyl, aryl, heteroaryl, arylalkyl or (hetereoaryl)alkyl wherein said alkyl, alkenyl, alkynyl, cycloalkyl, (cycloalkyl)alkyl, aryl, heteroaryl, arylalkyl and (heteroaryl)alkyl groups are optionally substituted with bromo, iodo, $OR^d$, $SR^e$, 1–3 $C_{1-3}$alkyl, 1–3 chloro or 1–5 fluoro;

$R^a$, $R^b$, and $R^c$ are independently selected from $C_{1-8}$alkyl, $O(C_{1-8}$alkyl) and phenyl;

$R_d$ is a removable hydroxyl protecting group, $C_{1-10}$alkyl, benzyl or phenyl, wherein said phenyl group is optionally substituted with 1–3 substituents independently selected from $C_{1-4}$alkyl, $O(C_{1-4}$alkyl), $NH(C_{1-4}$alkyl), $N(C_{1-4}$alkyl)$_2$, or halo;

$R^e$ is $C_{1-10}$alkyl or phenyl, wherein said alkyl group is optionally substituted with a group selected from $O(C_{1-4}$alkyl), $NH(C_{1-4}$alkyl), $N(C_{1-4}$alkyl)$_2$, phenyl or 1–5 fluoro, and wherein said phenyl group is optionally substituted with 1–3 substituents independently selected from $C_{1-4}$alkyl, $O(C_{1-4}$alkyl), $NH(C_{1-4}$alkyl), $N(C_{1-4}$alkyl)$_2$ or halo;

$R^f$ is $C_{1-10}$alkyl or phenyl, wherein said phenyl group is substituted with 1–3 substituents independently selected from $C_{1-4}$alkyl, $O(C_{1-4}$alkyl), $NH(C_{1-4}$alkyl), $N(C_{1-4}$alkyl)$_2$ or halo;

or $R^e$ and $R^f$, whether or not on the same atom, can be taken together with any attached and intervening atoms to form a 4–7 membered ring;

$R^g$ is $NR^eR^f$, $OR^d$, $NR^e(C=O)R^f$, $CONR^eR^f$, $SO_2NR^eR^f$ or a 4–9 membered mono- or bicyclic N-heterocycloalkyl ring that can be optonally substituted with 1–3 $C_{1-3}$ alkyl and can be optionally interrupted by O, S or $NR^e$;

L is $CH_2$, $CR^eR^f$, or $C_{2-6}$ alkylene, wherein said alkylene linker can be optionally interrupted by O, S or $NR^e$;

M is O, S, $NR^e$, $NR^e(C=O)$ or $(C=O)NR^e$;

and n is one, two or three.

2. The process of claim 1 wherein the alkylation is performed with an alkylating agent of formula VII in the presence of a base,

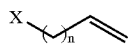

VII wherein X is Br, Cl, I, OMs, OTs or OTf.

3. The process of claim 2 wherein the base is sodium hydride, potassium hydride, lithium diisopropylamide, lithium bis(trimethylsilyl)amide or sodium bis(trimethylsilyl)amide.

4. The process of claim 2 wherein the base is sodium hydroxide or potassium hydroxide, and wherein said base is in the presence of a chiral phase transfer catalyst selected from N-benzylcinchoninium bromide, N-(p-trifluorobenzyl)cinchoninium bromide, N-(3,4-dichlorobenzyl)cinchoninium chloride, N-benzylcinchonidinium bromide, N-(p-trifluorobenzyl)cinchonidinium bromide or N-(3,4-dichlorobenzyl)cinchonidinium chloride.

5. The process of claim 1 wherein the nucleophilic addition is performed with an alkenyl metal species of formula VIII,

VIII wherein M' is MgBr, Li or Ce.

6. The process of claim 1 wherein the ring closing olefin metathesis reaction is in the presence of a transition metal catalyst.

7. The process of claim 6 wherein the transition metal catalyst is

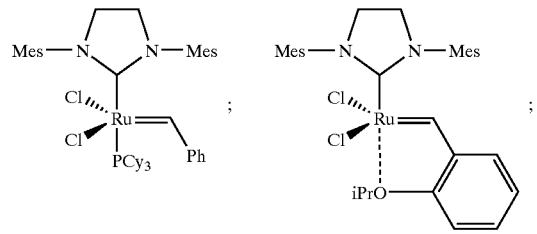

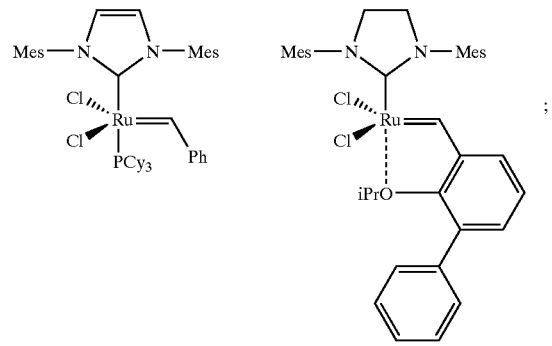

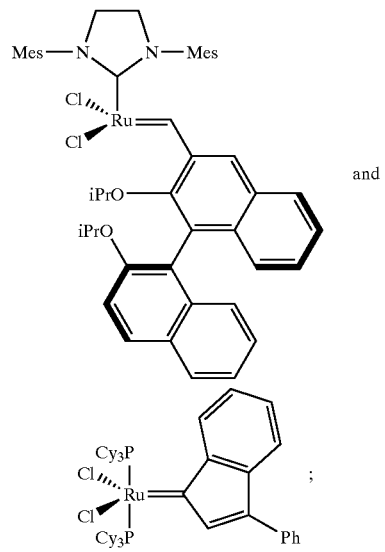

wherein

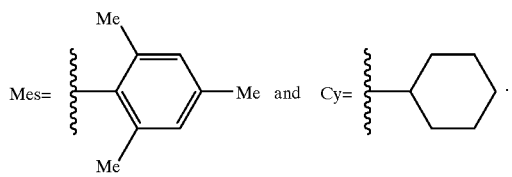 and 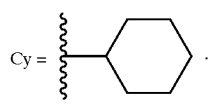

8. The process of claim 1 wherein the ring closing olefin metathesis reaction is in the presence of a chiral metathesis catalyst, wherein said chiral metathesis catalyst is

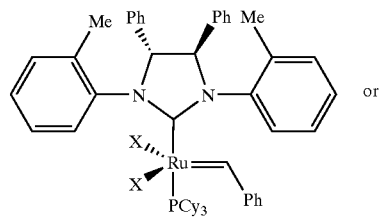 or

X = Cl, Br or I

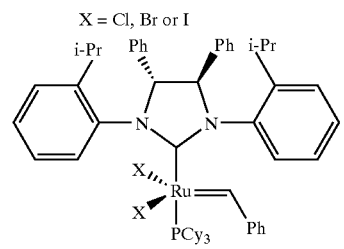

X = Cl, Br or I wherein

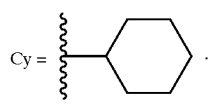

9. The process of claim 6 wherein the ring closing olefin metathesis reaction is in the presence of ethylene.

10. The process of claim 1 wherein the allylic oxidative rearrangement is performed with a chromium (IV) oxidant.

11. The process of claim 10 wherein the chromium (IV) oxidant is pyridinium chlorochromate, pyridinium dichromate, chromium trioxide or chromium trioxide-pyridine complex.

12. A process for making compounds of formula IA:

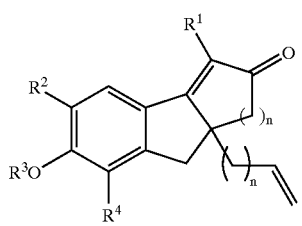

comprising the steps of:

a. alkylating an indanone of formula IIA to yield an intermediate of formula IIIA;

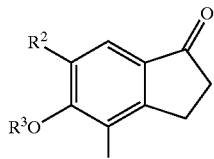

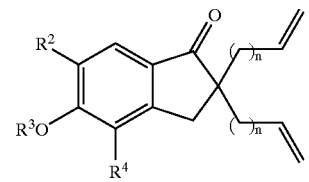

b. adding a nucleophile to the intermediate of formula IIIA to yield a diene of formula IVA;

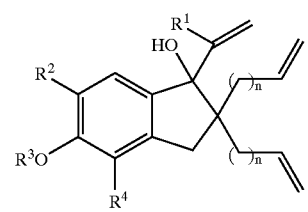

c. cyclizing the compound of formula IVA via a ring closing olefin metathesis reaction to yield an allylic alcohol of formula VA;

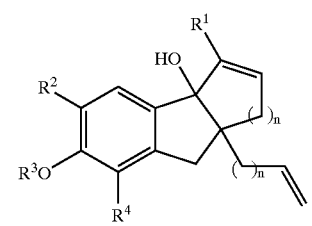

d. rearranging the compound of formula VA via an allylic oxidative rearrangement to yield an enone of formula VIA

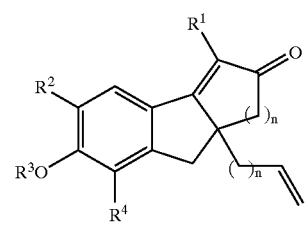

e. optionally deprotecting $R^3$;

wherein $R^1$ is hydrogen, $C_{1-10}$ alkyl, $C_{3-7}$ cycloalkyl, (cycloalkyl)alkyl, aryl, heteroaryl, arylalkyl, (heteroaryl)alkyl or $SiR^aR^bR^c$ wherein said alkyl, cycloalkyl, aryl and heteroaryl groups are optionally substituted with 1, 2 or 3 groups selected from fluoro, chloro, bromo, iodo, $OR^d$, $NR^eR^f$, $O(C=O)NR^eR^f$, $NR^e(C=O)R^f$, $NR^e(C=O)OR^f$, $SR^e$, $S(O)R^e$, $SO_2R^e$, $SO_2NR^eR^f$, $LR^g$ or $MLR^g$;

R² is hydrogen, fluoro, chloro, bromo, iodo, methyl or CF₃;

R³ is hydrogen, C₁₋₁₀ alkyl, benzyl or a removable hydroxyl protecting group;

R⁴ is hydrogen, fluoro, chloro, bromo, iodo, methyl or CF₃;

$R^a$, $R^b$ and $R^c$ are independently selected from C₁₋₈alkyl, O(C₁₋₈alkyl) and phenyl;

$R_d$ is a removable hydroxyl protecting group, C₁₋₁₀alkyl, benzyl or phenyl, wherein said phenyl group is optionally substituted with 1–3 substituents independently selected from C₁₋₄alkyl, O(C₁₋₄alkyl), NH(C₁₋₄alkyl), N(C₁₋₄alkyl)₂ or halo;

$R^e$ is C₁₋₁₀alkyl or phenyl, wherein said alkyl group is optionally substituted with a group selected from O(C₁₋₄alkyl), NH(C₁₋₄alkyl), N(C₁₋₄alkyl)₂, phenyl or 1–5 fluoro, and wherein said phenyl group is optionally substituted with 1–3 substituents independently selected from C₁₋₄alkyl, O(C₁₋₄alkyl), NH(C₁₋₄alkyl), N(C₁₋₄alkyl)₂ or halo;

$R^f$ is C₁₋₁₀alkyl or phenyl, wherein said phenyl group is substituted with 1–3 substituents independently selected from C₁₋₄alkyl, O(C₁₋₄alkyl), NH(C₁₋₄alkyl), N(C₁₋₄alkyl)₂ or halo;

or $R^e$ and $R^f$, whether or not on the same atom, can be taken together with any attached and intervening atoms to form a 4–7 membered ring;

$R^g$ is $NR^eR^f$, $OR^d$, $NR^e(C=O)R^f$, $CONR^eR^f$, $SO_2NR^eR^f$ or a 4–9 membered mono- or bicyclic N-heterocycloalkyl ring that can be optonally substituted with 1–3 C₁₋₃ alkyl and can be optionally interrupted by O, S or $NR^e$;

L is CH₂, $CR^eR^f$, or C₂₋₆ alkylene, wherein said alkylene linker can be optionally interrupted by O, S or $NR^e$;

M is O, S, $NR^e$, $NR^e(C=O)$ or $(C=O)NR^e$;

and n is one, two or three.

13. The process of claim 12 wherein the alkylation is performed with an alkylating agent of formula VII in the presence of a base,

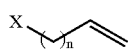

VII wherein X is Br, Cl, I, OMs, OTs or OTf.

14. The process of claim 13 wherein the base is sodium hydride, potassium hydride, lithium diisopropylamide, lithium bis(trimethylsilyl)amide or sodium bis(trimethylsilyl)amide.

15. The process of claim 12 wherein the nucleophilic addition is performed with an alkenyl metal species of formula VIII,

VIII wherein M' is MgBr, Li or Ce.

16. The process of claim 12 wherein the ring closing olefin metathesis reaction is in the presence of a transition metal catalyst.

17. The process of claim 16 wherein the transition metal catalyst is

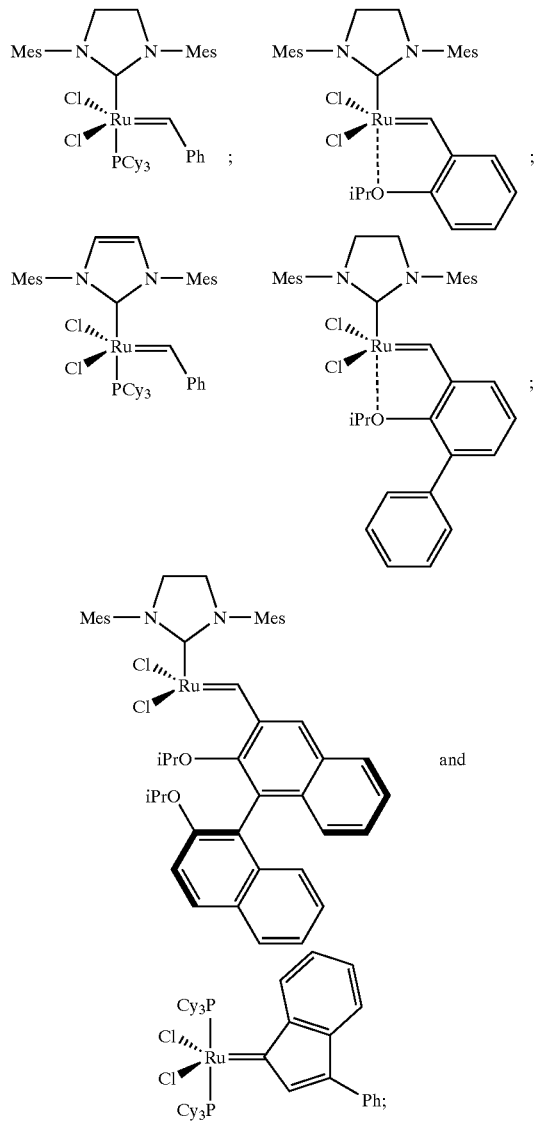

and wherein

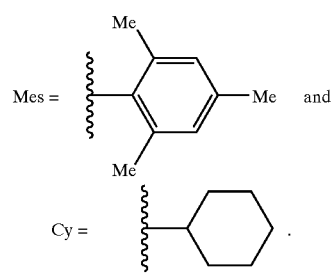

18. The process of claim 16 wherein the ring closing olefin metathesis reaction is in the presence of ethylene.

19. The process of claim 12 wherein the ring closing olefin metathesis reaction is in the presence of a chiral metathesis catalyst, wherein said chiral metathesis catalyst is

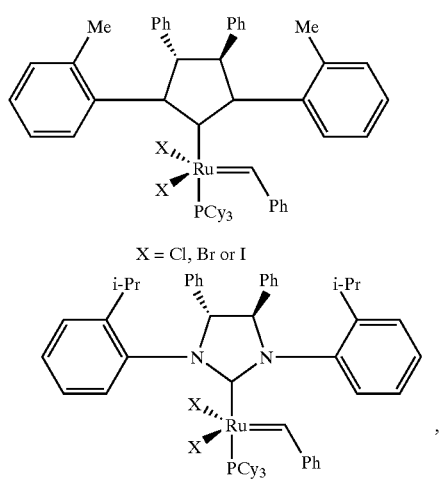
X = Cl, Br or I
or
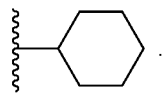
wherein
20. The process of claim 12 wherein the allylic oxidative rearrangement is performed with a chromium (IV) oxidant.
21. The process of claim 20 wherein the chromium (IV) oxidant is pyridinium chlorochromate, pyridinium dichromate, chromium trioxide or chromium trioxide-pyridine complex.
* * * * *